United States Patent [19]

Machek

[11] Patent Number: 4,895,168
[45] Date of Patent: Jan. 23, 1990

[54] GUIDEWIRE WITH MOVABLE CORE AND EXTERNAL TUBULAR SAFETY COVER

[75] Inventor: James E. Machek, Bradfordwoods, Pa.

[73] Assignee: Schneider (USA) Inc., A Pfizer Company, Plymouth, Minn.

[21] Appl. No.: 146,701

[22] Filed: Jan. 21, 1988

[51] Int. Cl.⁴ .............................................. A61M 25/00
[52] U.S. Cl. .................................... 128/772; 128/657; 604/170
[58] Field of Search .................. 128/772, 656–658, 128/341; 604/164, 166, 170, 280, 282

[56] References Cited

U.S. PATENT DOCUMENTS

| | | | |
|---|---|---|---|
| 3,841,308 | 10/1974 | Tate | 128/772 |
| 3,922,378 | 11/1975 | Kline | 128/772 X |
| 3,973,556 | 8/1976 | Fleischhacker et al. | 128/772 |
| 4,003,369 | 1/1977 | Heilman et al. | 128/772 |
| 4,080,706 | 3/1978 | Heilman et al. | 128/772 X |
| 4,307,722 | 12/1981 | Evans | 128/341 X |
| 4,548,206 | 10/1985 | Osborne | 128/772 |
| 4,619,274 | 10/1986 | Morrison | 604/170 X |
| 4,676,249 | 6/1987 | Arenas et al. | 128/772 X |

OTHER PUBLICATIONS

"The SOS Open Ended Guide Wire from USCI, Application and Case Studies", published by C. R. Bard, Inc., 1985.

"SOS Interventional Wire Guides", published by Cook Inc., 1986.

*Primary Examiner*—Angela D. Sykes
*Attorney, Agent, or Firm*—Fleit, Jacobson, Cohn, Price, Holman & Stern

[57] ABSTRACT

A movable core guidewire assembly comprising a wire wound cylindrical casing having a distal closed end and a proximal open end, a resilient movable core wire extending inside the cylindrical casing between its proximal and distal ends, and a plastic safety cover coextensive with and surrounding the wire wound cylindrical casing. The plastic safety cover functions to retain fragments of a broken guidewire, replacing the interior safety wire used in prior art guidewire assemblies. Therefore, the movable core wire can utilize all the space inside the cylindrical casing to maximize the ability of medical personnel to manipulate the guidewire assembly inside the body. A specific procedure for forming a closed distal tip of the guidewire assembly from an initially open ended casing and safety cover is also disclosed.

21 Claims, 2 Drawing Sheets

GUIDEWIRE WITH MOVABLE CORE AND EXTERNAL TUBULAR SAFETY COVER

BACKGROUND OF THE INVENTION

The present invention relates to movable core guidewires, and more particularly relates to a guidewire having a distal closed end and a proximal open end and having a safety cover located thereon.

In medical procedures such as angiography, catheters must be positioned deep in the vascular system, and generally such catheters must reach difficult to access regions. In order to introduce such a catheter into the vascular system of a patient, a sharp cannula is inserted through the skin and into the vascular system, and then a spring guidewire is inserted through the cannula and advanced in the vascular system until its distal end reaches the location where the catheter tip is desired. The cannula is then removed from the patient's body and the catheter is inserted into the body by sliding it over the guidewire. The guidewire generally then is withdrawn, and the catheter is ready for use. Catheters are also used in non-vascular procedures such as urinary tract procedures, and are introduced as described above.

As used herein, the terms "catheter" and "guidewire" are meant to encompass all types of catheters and guidewires. Fog convenience, however, the specific examples discussed herein relate to procedures dealing with the vascular system. Nevertheless, the present invention is not limited to catheters and guidewires designed for the vascular system, and the benefits and advantages of the present invention apply equally to any medical procedure where a catheter must be introduced through the skin and reach a remote location in the human body.

The specific type of guidewire forming the present invention is the movable core guidewire. This type of guidewire generally is more flexible and steerable than the fixed core guidewire, and hence can be used in more difficult to reach locations of the body.

The core wire of the movable guidewire assembly provides a degree of strength, rigidity, and steerability such that the entire assembly can negotiate the vascular system. And it is known that the flexibility of the guidewire assembly can be altered by changing the flexibility of the core wire along the length thereof. Furthermore, with the movable core guidewire, the flexibility of the guidewire assembly at the tip can be altered by moving the core wire into and out of the guidewire distal end.

Structural integrity is another requisite for a successful guidewire. A broken guidewire, with the possibility of leaving debris in a patient's body, cannot be tolerated. A commonly employed precaution against leaving a broken guidewire tip in the vascular system of a patient, is the provision of a thin wire, termed a safety wire, inside the wound outer guidewire casing. The safety wire is customarily connected to both the proximal and distal ends of the guidewire to enable the removal of any broken fragments, should a break occur in the outer spring of the guidewire assembly. One disadvantage of the internal safety wire is that it occupies space in the interior of the guidewire. Furthermore, should there be a break in the guidewire, there would be jagged edges exposed at the position of the break, and hence there would be a risk of tearing tissue as the broken guidewire is retracted from the body.

Some guidewire assemblies having distal closed ends and proximal open ends use a safety wire of a circular cross section, such as that described in U.S. Pat. No. 4,548,206 to Osborne. Additionally, it recently has been proposed that the safety wire conform to the shape of the guidewire lumen on one of its surfaces; see commonly assigned U.S. patent application Ser. No. 061,146, filed June 12, 1986, disclosing a crescent-shaped safety wire. In these types of guidewire assemblies, the mere presence of the safety wire inside the lumen makes movement of the core wire more difficult.

Reference also is directed to a publication entitled "The SOS Open Ended Guide Wire From U.S.C.I. Application and Case Study", published by C. R. Bard, Inc., 1985, and a publication entitled "SOS Interventional Wire Guides", published by Cook Inc., 1986. In both of these publications, there are disclosed catheters utilizing movable core wires, wherein the catheters are open at both ends to perform injection and infusion functions. The catheters are coated on their exterior surfaces.

With these types of SOS interventional devices, there are disadvantages associated with guidewire usage. Specifically, with open ends, blood can enter the open tip of the catheter and form a clot which subsequently could be pushed out of the catheter into the vascular system by the core wire. In addition, once the catheter is used for infusion, a core wire can no longer be inserted into and manipulated in the lumen for performing guidewire functions. Furthermore, because the SOS devices are designed primarily for infusion, the core wires are relatively difficult to manipulate in the catheter structure.

The movable core closed end guidewire assembly of the present invention utilizes a safety cover that overcomes the above disadvantages of known closed end guidewire assemblies.

OBJECTS OF THE INVENTION

An object of the present invention is to provide a closed end movable core guidewire assembly in which wasted space in the interior of the guidewire assembly is eliminated.

Another object of the present invention is to provide a closed end movable core guidewire assembly having increased maneuverability of the core wire.

Still a further object of the present invention is to provide a closed end movable core guidewire assembly having increased available space for the core wire to facilitate manipulation by the medical personnel in control of the guidewire assembly.

Another object of the present invention is to provide a closed end movable core guidewire assembly with a safety cover that facilitates movement of the core wire in the guidewire casing without sacrificing the strength or the structural integrity of the guidewire assembly.

Another object of the present invention is to provide a closed end movable core guidewire assembly having a safety cover which prevents the tearing of tissue with exposed jagged edges, should the guidewire break during a procedure.

SUMMARY OF THE INVENTION

Briefly stated, the present invention relates to a movable core guidewire assembly having an elongated wire would cylindrical casing, a distal closed end and a proximal open end. A thin plastic safety cover having a corresponding closed distal end and an open proximal end surrounds the cylindrical casing.

The plastic safety cover is coextensive with the cylindrical casing and functions as a safety wire by capturing guidewire fragments should the guidewire break while inside the body. Furthermore, the plastic safety cover does not occupy any space inside the guidewire assembly, hence providing maximum area within the guidewire casing for the movable core wire.

The cylindrical casing and safety cover initially have open distal ends. The safety cover is of the heat shrinkable type. When forming a closed distal tip, a plastic bead is partially inserted into the casing and the assembly is heated to allow the bead to seal the casing and the safety cover to shrink around the casing to completely seal the distal end of the guidewire assembly.

DESCRIPTION OF THE PREFERRED EMBODIMENT

Figure 1:
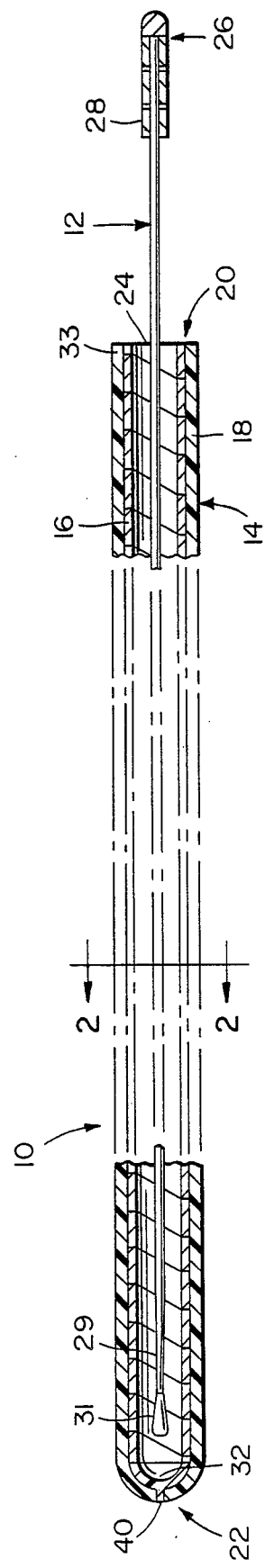
FIG. 1 illustrates a closed end guidewire assembly with a partially withdrawn, movable core wire and an exterior plastic safety cover.
Figure 2:
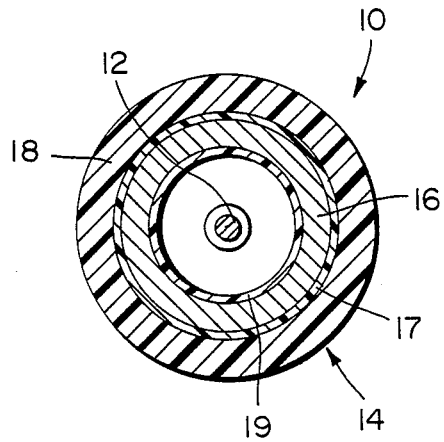
FIG. 2 is a cross section of the guidewire assembly taken through line 2—2 in FIG. 1.

Referring to FIGS. 1 and 2, the guidewire assembly in accordance with the preferred embodiment of the present invention is shown generally at 10. Particularly, the guidewire assembly 10 includes a core wire 12 movable in a casing assembly 14.

The casing assembly 14 includes a wound casing 16 surrounded by a thin plastic safety cover 18 extending between the proximal end 20 and the distal end 22 of the assembly 14. As can be seen in FIG. 1, the wound casing 16 and the plastic safety cover 18 are closed at distal end 22. The wound casing 16 takes the form of a coil spring which is developed from a wound wire, such as a rectangular cross section flat wire. The inner surface of casing 16 can be made ultra smooth by coating the base flat wire with a lubricating agent, such as Teflon, prior to being spring wound. Also, the surface of the casing can be lightly ground by abrasion and subsequently electro-polished. Further descriptions of specific casing assemblies can be found in U.S. Pat. Nos. 4,003,369 and 4,080,706 by Heilman et al, assigned to the assignee of the present invention.

The outer casing 16 of the guidewire assembly 10 is very flexible; therefore, to provide the desired degree of rigidity and steerability, the core wire 12 is inserted into an open ends 24 at the proximal end 20 of the casing assembly 14. The core wire 12 includes, at its proximal end 26, a cylindrical handle 28 such that the medical personnel can insert, withdraw and twist the core wire 12 relative to the casing 16 of the guidewire assembly 10. The distal end of core wire 12 may be tapered, as shown at 29, to provide more flexibility at the distal tip than over the remainder of the length, and may also include an enlarged tip 31 to prevent the core wire from exiting the casing 16 of the guidewire assembly 10. It is contemplated that the core wire 12 be either straight throughout its length or include a curved section at its distal end to facilitate steering; and core wire 12 can be coated with a lubricating agent, such as Teflon, to facilitate smooth movement within casing 16.

The plastic safety cover 18 is substantially coextensive with the casing 16 and is securely attached, as by being shrunk around the external surface of the casing 16 along its length between ends 20 and 22.

Figure 3:
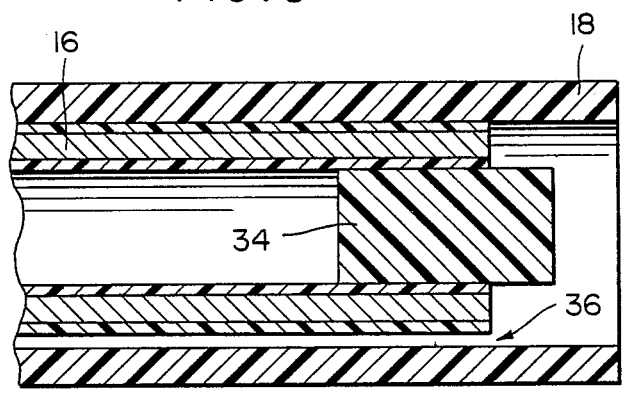
FIG. 3 is an enlarged cross section of the distal end of the guidewire assembly during one stage of the manufacturing operation.
Figure 4:
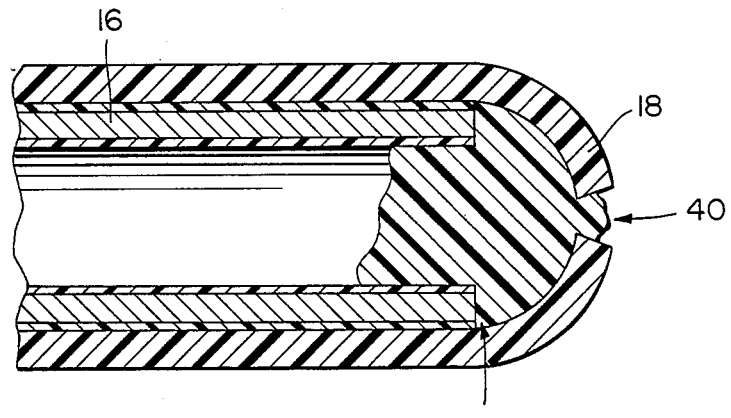
FIG. 4 is a cross section similar to that of FIG. 3, but showing the finished distal end of the guidewire assembly.

As best seen in FIG. 3, a low temperature melt beading or plug 34 of FEP Teflon is inserted into the distal open end of the casing 16 so that the plug extends slightly out of the end of the casing 16. The safety tube 18 formed of smooth TFE Teflon is of the heat shrinkable type and has a higher melting temperature than the plug 34. Therefore, initially the safety tube 18 has a sufficiently larger diameter than the casing 16 to facilitate sliding of the safety tube 18 over the casing 16 in the initial stages of construction. As a result a gap 36 is created between the casing 16 and the tube 18. Heat is then applied to the distal tip area of the guidewire 10 so that the tube 18 shrinks around the casing 16 and the plug 34 melts to form a seal 38 and closed tip 40 as shown in FIG. 4.

Although the dimensions of the guidewire 10 will vary depending upon its use, it is envisioned the outside diameter of the guidewire 10 will range from 0.045" to 0.032". Three preferable sizes of 0.038", 0.035" and 0.032" are contemplated. The inner diameter of the guidewire 10 ranges from 0.036" to 0.016", with specific diameters of 0.022", 0.018", and 0.016" corresponding to the three above preferable outer diameters, respectively. The preferred thickness of the plastic cover is on the order of 0.004". The diameter of the core wire 12 ranges from 0.020" to 0.010" with specific diameters of 0.017", 0.014", and 0.011" corresponding to the above three outer diameters, respectively.

In operation, the guidewire assembly 10 is inserted into the body as previously described. By manipulating core wire 12, the guidewire assembly 10 can negotiate the torturous path through the vascular system, or other systems. The degree of rigidity of the guidewire assembly 10 is primarily dependent upon the rigidity or flexibility of core wire 12, and upon the relative position of the core wire 12 within the casing 16. In the event that the guidewire 10 breaks while in the body, it is removed from the body with the broken fragments contained in the plastic safety cover 18. Further, as a broken guide wire of the present invention is withdrawn from the body, there is no risk of tearing tissue inside the body as a result of jagged broken edges.

With the exterior plastic safety cover 18 of the present invention, maximum space is provided within the guidewire assembly 10. Therefore, the movable core wire 12 has more room to slide and maneuver inside the casing assembly 14, giving the medical personnel a greater ability to manipulate the guidewire assembly 10 in a patient's body. Furthermore, the smooth coating on the inner surface of the casing 16 allows the use of core wires of variable stiffnesses and preformed shapes to perform specific guidewire manipulation techniques. In addition, the thickness of a plastic cover 18 is so small that the overall cross-sectional area of the guidewire assembly is not substantially increased. Along with excellent maneuverability, the closed end guidewire 10 is extremely anti-thrombogenic and has a low coefficient of friction due to the smooth outside covering 18.

It is understood that the above description is intended by way of example only and is not intended to limit the present invention in any way except as set forth in the following claims.

What is claimed is:

1. A movable core guidewire assembly absent an internal safety wire, said guidewire assembly comprising:

an elongated cylindrical casing having a distal closed end and a proximal open end;

an elongated resilient core wire movably positioned in said cylindrical casing; and an elongated plastic safety cover coextensive with and surrounding the cylindrical casing, having a distal closed end positioned at the distal end of said casing and a proximal open end positioned at the proximal end of the casing, said safety cover serving as an internal safety wire retaining any broken fragments of the guidewire in the event that the guidewire breaks inside the body of a patient. the space inside the casing that would be required by an internal safety wire being eliminated.

2. The movable core guidewire assembly of claim 1, wherein said cylindrical casing has an inner diameter of 0.016" to 0.036".

3. The movable core guidewire assembly of claim 1, wherein said cylindrical casing has an outer diameter of 0.032" to 0.045".

4. The movable core guidewire assembly of claim 1, wherein said plastic safety cover has a thickness of 0.0015" to 0.006".

5. The movable core guidewire assembly of claim 1, wherein said inner surface of said cylindrical casing is coated with a lubricating agent.

6. The movable core guidewire assembly of claim 1, wherein said core wire is coated with a lubricating agent.

7. The movable core guidewire assembly of claim 1, wherein said casing is developed from a spiral wound continuous wire.

8. The movable core guidewire assembly of claim 7, wherein said wire is rectangular in cross section.

9. The movable core guidewire assembly of claim 8, whereins aid wire is Teflon coated before being wounded.

10. A movable core guidewire assembly absent an internal safety wire, said guidewire assembly comprising:

an elongated cylindrical casing initially open at both distal and proximal ends and developed from a spiral wound continuous wire;

an elongated resilient core wire positioned in said cylindrical casing, having a distal end positioned at the distal end of said casing, and having a proximal and extending outside said proximal end of said casing;

an elongated heat shrinkable cylindrical plastic safety cover coextensive with and surrounding the cylindrical casing, and initially having a distal open end positioned at the distal end of said casing and a proximal open end positioned at the proximal end of said casing, said safety cover serving as an internal safety wire retaining any broken fragments of the guidewire in the event that the guidewire breaks inside the body of a patient, the space inside the casing that would be required by an internal safety wire being eliminated;

a plastic plug having a lower melting temperature than that of said safety cover partially inserted into the distal end of said casing so that when the distal end of said guidewire assembly is heated, the safety cover shrinks firmly around the cylindrical casing and the plug melts to form a sealed and closed distal tip.

11. The movable core guidewire assembly of claim 10, wherein said safety cover is formed of the TFE type of Teflon.

12. The movable core guidewire assembly of claim 10 wherein said plug is formed of FEP type of Teflon.

13. The movable core guidewire assembly of claim 10, wherein said cylindrical casing has an inner diameter of 0.016" to 0.036".

14. The movable core guidewire assembly of claim 10, wherein said plastic safety cover has a thickness of 0.015" to 0.006".

15. The movable core guidewire assembly of claim 10, wherein the inner surface of said cylindrical casing is coated with a lubricating agent.

16. The movable core guidewire assembly of claim 10, wherein said core wire is coated with a lubricating agent.

17. The movable core guidewire assembly of claim 10, wherein the distal end of said core wire is tapered.

18. The movable core guidewire assembly of claim 10, wherein the distal end of said core wire terminates in an enlarged tip.

19. The movable core guidewire of claim 18, wherein said wire is Teflon coated before being wound.

20. The movable core guidewire assembly of claim 10, wherein said spiral wound continuous wire is rectangular in cross section.

21. The movable core guidewire assembly of claim 10, wherein said cylindrical casing has an outer diameter of 0.032" to 0.045".

* * * * *